(12) United States Patent
Michejda

(10) Patent No.: US 7,883,698 B2
(45) Date of Patent: Feb. 8, 2011

(54) ISOLATION AND PRESERVATION OF FETAL HEMATOPOIETIC AND MESENCYMAL SYSTEM CELLS FROM NON-CONTROVERSIAL MATERIALS AND/OR TISSUES RESULTING FROM MISCARRIAGES AND METHODS OF THERAPEUTIC USE

(76) Inventor: Maria Michejda, 13814 Hidden Glen La., N. Potomac, MD (US) 20878

( * ) Notice: Subject to any disclaimer, the term of this patent is extended or adjusted under 35 U.S.C. 154(b) by 0 days.

(21) Appl. No.: 11/654,737

(22) Filed: Jan. 17, 2007

(65) Prior Publication Data

US 2008/0171019 A1    Jul. 17, 2008

(51) Int. Cl.
*A01N 63/00* (2006.01)
*A01N 1/02* (2006.01)
(52) U.S. Cl. ......................................... 424/93.7; 435/13
(58) Field of Classification Search ........................ None
See application file for complete search history.

(56) References Cited

U.S. PATENT DOCUMENTS

| | | | |
|---|---|---|---|
| 5,004,681 A | | 4/1991 | Boyse et al. |
| 5,118,512 A | * | 6/1992 | O'Leary et al. ............... 435/1.1 |
| 5,192,553 A | | 3/1993 | Boyse et al. |
| 6,143,289 A | | 11/2000 | Broxmeyer et al. |
| 6,461,645 B1 | | 10/2002 | Boyse et al. |
| 6,613,568 B2 | | 9/2003 | Kaufman et al. |
| 6,887,706 B2 | | 5/2005 | Zhang et al. |
| 6,987,102 B2 | | 1/2006 | Bridger et al. |
| 7,005,252 B1 | | 2/2006 | Thomson |
| 7,029,913 B2 | | 4/2006 | Thomson |
| 2005/0106554 A1 | * | 5/2005 | Palecek et al. .................. 435/2 |
| 2005/0255592 A1 | * | 11/2005 | Collins et al. ................ 435/372 |

OTHER PUBLICATIONS

Rogers et al. (Cytotherapy. 2001; 3: 269-276).*
Chan et al (Progress in Obstetrics and Gynaecology 17. Sep. 2006. Developmental Stem Cell Therapy, Chapter 2. pp. 15-30).*
Jones et al. (Bone Marrow Transplantation. 2004; 33: 1061-1063).*
Michejda et al. (Transplantation. Aug. 1981; 32(2): 96-100).*
Hunt CJ et al Cryo Letters 27: 73-86 (2006).

* cited by examiner

*Primary Examiner*—Scott Long
(74) *Attorney, Agent, or Firm*—Rashida A. Karmali

(57) ABSTRACT

The present invention is directed to compositions of fetal hematopoietic stem and progenitor cells and stromal (mesencymal) cells derived from second trimester (16-20 weeks gestation) miscarriages, that are isolated, processed and cryopreserved, and the therapeutic uses of such stem and progenitor cells upon application. Such compositions may be useful for hematopoietic reconstitution and/or replacement in patients with various diseases and metabolic disorders. The invention also relates to methods for collecting, isolating, processing and cryopreserving of the fetal stem and progenitor cells of the invention. Importantly, the invention meets an urgent need in regenerative medicine while at the same time ensures utility of the product compositions because it utilizes fetal materials from second trimester (16-20 weeks of gestation) spontaneously lost pregnancies which are free of moral or ethical burdens.

1 Claim, No Drawings

ISOLATION AND PRESERVATION OF FETAL HEMATOPOIETIC AND MESENCYMAL SYSTEM CELLS FROM NON-CONTROVERSIAL MATERIALS AND/OR TISSUES RESULTING FROM MISCARRIAGES AND METHODS OF THERAPEUTIC USE

1. FIELD OF INVENTION

The present invention is directed to compositions of hematopoietic stem and progenitor cells and tissues of fetal origin, that are isolated, processed and cryopreserved, and the therapeutic uses of such stem and progenitor cells upon application. Such compositions may be useful for hematopoietic reconstitution and/or replacement in patients with various diseases and metabolic disorders. The invention also relates to methods for collecting, isolating, processing and cryopreserving of the fetal stem and progenitor cells of the invention. Importantly, the invention meets an urgent need while at the same time ensures utility of the product compositions because it utilizes fetal materials from second trimester (16-20 weeks of gestation) spontaneously lost pregnancies which are free of moral or ethical burdens.

2. BACKGROUND TO THE INVENTION

The present invention resides generally in the field of regenerative medicine using hematopoietic stem and progenitor cells. More particularly, the present invention relates to hematopoietic reconstitution and replacement in patients with various diseases and metabolic disorders. Regenerative medicine is a newly evolving method of targeted treatments of a large number of life threatening diseases. It involves three therapeutic technologies—cellular therapy, cell engineering and gene therapy—all three involved in the utilization of human tissues.

Cellular therapy has the broadest therapeutic applications in various diseases such as immunodeficiencies, hemoglobinopathies, metabolic disorders, diseases of the nervous system and some malignancies.

Cell engineering is another promising area of novel therapy that may have a major impact on management of cardiac ischemic diseases, treatment of bone and joint diseases, and chronic wounds with bone marrow or mesenchymal stem cells.

Gene therapy is another form of technology that has held considerable promise although unexpected long term effects of gene therapy, such as malignancies and death have limited its clinical application.

Cellular therapies as well as cell engineering, the most important technologies in regenerative medicine, require a large supply of stem cells. At present there is an insufficient supply of human stem cells for current applications and this lack will be compounded as the regenerative medicine reaches its full potential. The current sources of human hematopoietic stem cells include adult peripheral blood, cord blood, and the adult bone marrow. The morphologically recognizable and functionally capable cells circulating in blood include erythrocytes, neutrophilic, eosinophilic, and basophilic granulocytes, B-, T-, nonB-, non T-lymphocytes, and platelets. These mature cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets. The precursor cells derive from more primitive cells that can simplistically be divided into two major subgroups: stem cells and progenitor cells. The definitions of stem and progenitor cells are operational and depend on functional, rather than on morphological, criteria. Stem cells have extensive self-renewal or self-maintenance capacity, a necessity since absence or depletion of these cells could result in the complete depletion of one or more cell lineages, events that would lead within a short time to disease and death. Some of the stem cells differentiate upon need, but some stem cells or their daughter cells produce other stem cells to maintain the precious pool of these cells. Thus, in addition to maintaining their own kind, pluripotent stem cells are capable of differentiating into several sublines of progenitor cells with more limited or no self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways.

Under the appropriate growth conditions, the stem or progenitor cells will go through a sequence of proliferation and differentiation yielding mature end stage progeny, which thus allows the determination of the cell type giving rise to the colony. If the colony contains granulocytes, macrophages, erythrocytes, and megakaryocytes (the precursors to platelets), then the cells giving rise to them would have been pluripotent cells. To determine if these cells have self-renewal capacities, or stemness, and can thus produce more of their own kind, cells from these colonies can be replated in vivo or in vitro. Those colonies, which upon replating into secondary culture plates, give rise to more colonies containing cells of multilineages, would have contained cells with some degree of stemness. The stem cell and progenitor cell compartments are themselves heterogeneous with varying degrees of self-renewal or proliferative capacities. Self-renewal would appear to be greater in those stem cells with the shortest history of cell division, and this self-renewal would become progressively more limited with subsequent division of the cells.

Reconstitution of the hematopoietic system has been accomplished by bone marrow transplantation. The stem and progenitor cells in donated bone marrow can multiply and replace the blood cells responsible for protective immunity, tissue repair, clotting, and other functions of the blood. In successful bone marrow transplantation, the blood, bone marrow, spleen, thymus and other organs of immunity are repopulated with cells derived from the donor.

Cryopreservation of Cells—Freezing and thawing are destructive to most living cells. Upon cooling, as the external medium freezes, cells equilibrate by losing water, thus increasing intracellular solute concentration. Below about −10-15° C., intracellular freezing will occur. Both intracellular freezing and solution effects are responsible for cell injury. It has been proposed that freezing destruction from extracellular ice is essentially a plasma membrane injury resulting from osmotic dehydration of the cell. Cryoprotective agents and optimal cooling rates can protect against cell injury. Cryoprotection by solute addition is thought to occur by two potential mechanisms: by penetration into the cell, reducing the amount of ice formed; or kinetically, by decreasing the rate of water flow out of the cell in response to a decreased vapor pressure of external ice. Different optimal cooling rates have been described for different cells. Various groups have looked at the effect of cooling velocity or cryopreservatives upon the survival or transplantation efficiency of frozen bone marrow cells or red blood cells. The successful recovery of human bone marrow cells after long-term storage in liquid nitrogen has been described (1983, American Type Culture Collection, Quarterly Newsletter 3(4):1). There are many methods of cryopreservation and many cryoprotective cocktails have been proposed. However, the recovery of viable cells is still very poor (generally not better than 60%) (Hunt et al., Cryo Letters 2006, 27: 73-86). Experience with standard protocols based on those designed for cord blood stem cells have clearly indicated that there is need for further improvement in the procedures for cryopreservation. Moreover, it is known that standard freezing solutions that contain 10% dimethyl sulfoxide (DMSO), which routinely give 60% cell recovery after thawing, can induce neuro- and cardio-toxic reactions. Consequently the present invention fucusses effort in this area on minimizing the toxic effects of DMSO by radically decreasing its concentration in the freezing cocktail.

Gene Therapy refers to the transfer and stable insertion of new genetic information into cells for the therapeutic treatment of diseases or disorders. The foreign gene is transferred into a cell that proliferates to spread the new gene throughout the cell population. Thus stem cells, or pluripotent progenitor cells, are usually the target of gene transfer, since they are proliferative cells that produce various progeny lineages which will potentially express the foreign gene. Most studies in gene therapy have focused on the use of hematopoietic stem cells. High efficiency gene transfer systems for hematopoietic progenitor cell transformation have been investigated for use. Reports on the development of viral vector systems indicate a higher efficiency of transformation than DNA-mediated gene transfer procedures (e.g., $Ca_3PO_4)_2$ precipitation and DEAE dextran) and show the capability of integrating transferred genes stably in a wide variety of cell types. Recombinant retrovirus vectors have been widely used experimentally to transduce hematopoietic stem and progenitor cells. Genes that have been successfully expressed in mice after transfer by retrovirus vectors include human hypoxanthine phosphoribosyl transferase. Bacterial genes have also been transferred into mammalian cells, in the form of bacterial drug resistance gene transfers in experimental models. Introduction of drug resistance genes into hematopoietic stem cells has been accomplished using a retroviral vector system. Adenovirus vectors have been used successfully to transduce mammalian cell lines to neomycin resistance. Other viral vector systems that have been investigated for use in gene transfer include parvoviruses and vaccinia viruses. Other methods of gene transfer including microinjection, electroporation, liposomes, chromosome transfer, and transfection techniques have been published in literature and are incorporated herein.

The promise of stem cell therapy through cellular, cell engineering and/or gene therapies, has generated tremendous hope for the development of new sources of embryonic stem cells, including cloning and creation of new embryonic stem cell lines. However, there are still very significant problems to overcome before embryonic stem cells can be utilized in therapy. Likewise the use of fetal stem cells derived from elective abortions is plagued with many problems. Most elective abortions occur early in gestation hence there are little or no hematopoeitic cells in long bones because they have still not translocated to their ultimate destination from the liver. Moreover, there are significant moral and ethical problems in using fetal tissue derived from elective abortions. The present invention has overcome some of these problems by establishing fetal stem cells from second trimester miscarriages. The second trimester fetal tissue has many advantages. The fetal tissue, especially the hematopoietic tissue, has the optimal characteristics for long term engraftment and regenerative properties. This is related to a very high number of transplantable primitive cells with high clonogenic and proliferative properties. Furthermore, in contrast to other sources of stem cells described in the prior art (U.S. Pat. No. 5,004,681 to E. A. Boyse et al; U.S. Pat. No. 5,192,553 to E. A. Boyse et al; U.S. Pat. No. 6,143,289 to Hal E. Broxmeyer et al; U.S. Pat. No. 6,461,645 E. A. Boyse et al; U.S. Pat. No. 6,613,568 to D. S. Kaufman et al; U.S. Pat. No. 6,887,706 to S-C Zhang et al; U.S. Pat. Nos. 6,987,102; 7,005,252 to James A Thomson; and U.S. Pat. No. 7,029,913 to James A. Thomson), the fetal cells in the present invention have very low immunogenicity because of the age of the specimen (16-20 weeks), where the immune system is still poorly developed. The therapeutic mechanism of the fetal stems of the invention, though not fully understood, may be related to cellular reconstitution, replacement of detected cells or enhancement of their function by release of endogenous trophic factors. Tissue derived from second trimester lost pregnancies is completely free from the moral and bioethical problems associated with other fetal or embryonic sources of stem cells because it is considered cadaveric tissue and is fully acceptable for use in therapy.

3. SUMMARY OF THE INVENTION

The present invention is directed to hematopoietic stem and progenitor cells and stromal (mesencymal) cells derived from fetal bone marrow collected from second trimester (16-20 weeks gestation) miscarriages, that are cryopreserved, and the therapeutic uses of such stem and progenitor cells upon thawing. In particular, the present invention relates to the therapeutic use of fetal or neonatal stem cells for hematopoietic (or immune) reconstitution. Hematopoietic reconstitution with the cells of the invention can be valuable in the treatment or prevention of various diseases and disorders such as anemias, malignancies, autoimmune disorders, and other immune dysfunctions and deficiencies.

In another embodiment, fetal hematopoietic stem and progenitor cells and stromal (mesencymal) cells derived from second trimester (16-20 weeks gestation) miscarriages which contain a heterologous gene sequence can be used for hematopoietic reconstitution in gene therapy.

In a preferred embodiment of the invention, fetal bone marrow cells derived from second trimester (16-20 weeks gestation) miscarriages that have been cryopreserved and thawed can be used for cellular reconstitution.

In a preferred embodiment of the invention, fetal bone marrow cells derived from second trimester (16-20 weeks gestation) miscarriages can be used for reconstitution directly after testing for compatibility and quality assurance.

The invention also relates to methods of collection and cryopreservation of the neonatal and fetal stem and progenitor cells of the invention

4. DETAILED DESCRIPTION OF THE INVENTION

The present invention is directed to fetal hematopoietic stem and progenitor cells and stromal (mesencymal) cells derived from second trimester miscarriages, directly or cryopreserved, and the therapeutic uses of such stem and progenitor cells upon thawing. In particular, the present invention relates to the use of fetal stem cells derived from second trimester miscarriages for hematopoietic reconstitution and/or defected cell replacement, and/or enhancement of endogenous growth factors.

In a preferred embodiment of the invention, the fetal stem cells derived from second trimester miscarriages can be used in hematopoietic reconstitution. In such an embodiment, the invention provides substantial advantages over the present use of adult bone marrow for hematopoietic reconstitution. Present use of adult bone marrow transplantation is severely restricted by the fact that there is virtually never a perfectly matched (genetically identical) donor, except in cases where an identical twin is available or where bone marrow cells of, for example, a cancer patient in remission are stored in the viable frozen state in the hope that they will be free of malignant cells and healthy enough to be returned to the patient for treatment of any future relapse. Except in such rare cases, the inevitable genetic mismatch that results can entail the serious and sometimes lethal complications of host versus graft or graft versus host disease. In order to avoid host rejection of the foreign bone marrow cells (host versus graft reaction), the patient must be immunologically incapacitated. Such immune incapacitation is itself a cause of serious complications. Furthermore, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

In an embodiment of the invention directed to the use of fetal stem and progenitor cells derived from second trimester miscarriages for hematopoietic reconstitution, there are several main reasons for preferring the use of such fetal cells to conventional bone marrow transplantation. First, no donor is required because the cells can be obtained from fetal tissue derived from second trimester miscarriages that would otherwise be discarded. Second, the complications arising in conventional bone marrow transplantation from the need for pretransplantation drug-induced or irradiation-induced immune incapacitation and from acute and chronic graft-versus-host disease are all eliminated because, in this embodiment, fetal stem cells have low immunogeneicity. For these reasons, present restrictions on the use of bone marrow transplantation arising from difficulties in finding even approximately matched donors, and from disease and mortality due to unavoidable genetic incompatibility, do not apply to reconstitution with fetal cells derived from second trimester miscarriages.

Furthermore, the prospects of success in bone marrow transplantation decline with age; although it is not clear whether the age of donor or patient is more important, it is proper to infer that younger (fetal) cells are preferable for hematopoietic reconstitution. Such fetal cells derived from second trimester miscarriages, have not been subjected to the "environmental outrage" that adult cells have undergone. Also, as an example of novel medical applications which may be feasible with fetal cells but not with conventional bone marrow transplantation, restoration with self cells taken at birth can be valuable in the treatment of disorders such as declining immune responsiveness and autoimmunity which occur in increasing frequency with age.

Many of the relative disadvantages discussed supra of the use of adult bone marrow cells for hematopoietic reconstitution, also apply to the use of adult peripheral blood for such reconstitution, and thus, the use of neonatal cells for hematopoietic reconstitution according to the present invention provides distinct advantages over the employment of adult bone marrow and peripheral blood stem cells. It has been implied that the ability of autologous peripheral adult blood to reconstitute the hematopoietic system, seen in some cancer patients, is associated with the far greater numbers of circulating progenitor cells in the peripheral blood produced after cytoreduction due to intensive chemotherapy and/or irradiation. However, there are possible detrimental effects, known or unknown, of prior chemotherapy or irradiation, on the stem and progenitor cell populations found in these patients.

There are additional reasons for preferring the use of fetal cells derived from second trimester miscarriages for hematopoietic reconstitution as provided by the present invention. Fetal tissue from that source is the preferred source of cells for hematopoietic reconstitution, since it is free from viral and microbial agents, known or unknown, latent or otherwise, that may be encountered in later life, other than those transmitted from the mother or during labor and delivery. In addition, in view of the extent to which the hematopoietic stem cell may possibly share with other cells the limitation in total number of cell divisions that it may undergo before senescence, it is proper to assume that the neonatal hematopoietic stem cell has a self-renewal and reconstituting capacity that is at least as great, and perhaps greater, than that of hematopoietic stem cells obtained at any later time in life.

The method of the invention may be divided into the following stages solely for the purpose of description: (a) collection of fetal tissues from second trimester miscarriages; (b) isolation of hematopoietic stem and progenitor cells and stromal (mesencymal) cells; (c) quality control and testing of fetal tissue; (d) cryopreservation; (e) recovery of stem and progenitor cells from the frozen state; (f) examination of thawed cells prior to clinical applications; and (g) therapeutic uses in reconstitution of the hematopoietic system.

Since fetal hematopoietic cells derived from second trimester miscarriages are envisioned for use in the present invention, descriptions and embodiments of the invention herein described for fetal cells derived from second trimester miscarriages.

The Properties of Fetal Tissue

Fetal tissues have unique biological and therapeutic properties, which are almost ideal for transplantation, for successful stem cell engraftments, as well as for reconstitution of generally defective cells. Human hematopoietic stem cells are pluripotent with a high capacity to differentiate into the complete repertoire of erythroid, myeloid and lymphoid cell lines. The fetus also has special immunologic characteristics that provide distinct advantages as a donor, as well as a recipient, for cellular and/or immune reconstitution and regeneration. During this time the human fetus has a "depleted" and not fully developed immunologic environment that is autologically primed to receive "homing" hematopoietic stem cells. Therefore bone marrow conditioning to provide space for transplanted stem cells in the fetus is not necessary in contrast to adult recipients. Immunological immaturity continues to the neonatal stage of development. Thus it has been long recognized that fetal tissue is pre-immunocompetent and is characterized by significantly reduced capacity to evoke immunogenic responses. This depressed immunocompetence or immunological immaturity results from ontogenic phenomena such as a reduced number or lack of post-thymic T-lymphocytes in utero, which when mature, contribute to reduced number or lack of post-thymic T-lymphocytes in utero. There is strong evidence that the human fetus is immunoincompetent up to 22 weeks of gestation, as judged by the generation of cytotoxic T-cell responses. It has been suggested that while T-cells may be found in circulation during pregnancy, they appear to be inactive. This ontogenic characteristic is due to the lack of expression of T-cell and NK-cell receptors, as well as the members of the LY-49 receptor family. Moreover, the fetus defends itself against rejection by catabolizing tryptophan, which suppresses T-cell activity. Fetal tolerance can be extended to infancy and it was observed that ABO incompatible heart transplantation during infancy results in full B-cell tolerance to donor blood group A and B antigens.

The subtle properties of stem cells are still poorly understood. It is however well established that most tissues contain small pools of stem cells. These cells may have a high capacity for self renewal, rapid cell division and they proliferate and differentiate into many lineages. These properties have raised great hopes for the utilization of stem cells in cellular and gene therapies. It has been suggested that stem cell research, including embryonic stem cells, will soon have profound implications on the future of medicine. However, recent results have challenged some of the overly enthusiastic claims in stem cell biology. Thus many reports on the plasticity of human adult hematopoietic stem cells (HSC) have been questioned. The lack of uniform standards for interpretation of results may have contributed to the controversy. What was understood as the unique plasticity of adult HSC may be simple cell fusion, hybrid formation and tetraploidy. There is new evidence that the adult marrow cells do not transdifferentiate into neural cells in vivo. The apparent lack of plasticity of adult HSC undermines many of the promised therapeutic applications. Similar challenges have appeared to the promised broad utilization of embryonic stem cells (ESC). For example, reports that ESCs secrete insulin were recently shown to be incorrect; the detected insulin came from the medium. The use of adult stem cells and ESCs in therapy will require caution and additional scrutiny. New discoveries in HSC biology should continuously refine the understanding of the functional properties of adult stem cells. Thus more in vivo studies are required to establish the efficacy of these cells for human therapies. In fact, the biological limitations of application of adult stem cells for therapy were recognized many years ago. Among these limitations are the small number of primitive cells, poor proliferative capacity, reconstitution and engraftment. The proliferative potential of adult HSCs decrease significantly with age due to the loss of telomeric repeat sequences and shortening of telomere lengths. Telomere length shortening ("replicative exhaustion") leads to decreased proliferation and functional capacity for engraftment. However these limitations do not appear to play a role in experimental cell engineering technology. The risks of application of ESCs to potential therapy are also well recognized. These include rapid and uncontrolled replication and differentiation that leads to tumor formation such as teratomas, and chromosomal mosaicism that is associated with genetic aberrations and post cloning gene imprinting. These problems must be solved before medical application. Each source of HSC has different intrinsic properties closely correlated with ontogenic changes that are vital determinants of phenotypic characteristics, lineage commitment, immunogenicity and proliferation. Consequently, the therapeutic potential of human hematopoietic stem cells is greatly influenced by the ontogeny of hematopoiesis.

The utilization of fetal HSCs derived from the fetal liver in the successful pioneering treatment of immunodeficiencies led us to our studies of fetal HSCs derived from $2^{nd}$ trimester (16-20 weeks) spontaneous abortions. We chose to work with fetal bone marrow rather than the liver because of its higher proliferative capacity, its significantly lower level of contamination and its higher post-cryopreservation viability that is sustained by the stromal microenvironment. Moreover, this new source of fetal stem cells is ethically non-controversial.

Fetal tissues have many unique properties such as rapid growth, cellular regeneration and self repair and are a promising source fetal stem cells in therapeutic transplantation. In view of the insufficiency of cells from currently used sources, additional sources are urgently needed. An epidemiological study on the incidence of spontaneous miscarriages showed that the number of miscarriages that could provide viable second trimester fetal tissue was very large. About 30% of miscarriages occur in the $2^{nd}$ trimester of which 15% (about 50,000 per year) represent viable healthy tissue. Specimens from $2^{nd}$ trimester are optimal for harvesting bone marrow cells because of the large volume of readily available, partially committed, immunocompetent cells which can be infused directly into patients without any preconditioning. However, these cells require a thorough screening for bacterial, viral and fungal contamination and genetic aberrations before their use in patients. The incidence of spontaneous miscarriages is on the increase in the industrialized world for various reasons.

In vivo xenograpfting studies of fetal hematopoietic stem cells utilizing a relevant primate model showed that fetal tissue has distinctive therapeutic properties that are optimal for transplantation. The phenotypic and functional characteristics of fetal bone marrow (FBM), adult bone marrow (ABM) and cord blood (CB) and peripheral blood (PB) sources of the most primitive stem/progenitor cells were studied. A stricking ontogenic difference in the proportion of CD34+ cells in FBM, ABM, PB and CB was observed (24.6% vs 2.1% vs 0.5% vs 2%). The clonogenic potential as measured by the CFU-C assay, was higher in FBM when compared with ABM, PB and CB, as well as proliferative responsiveness in the mixed lymphocyte reaction (MLR) assay of FBM and CB as compared to ABM and PB. The cytokinetic profiles of the cells from the four sources were also analyzed. This study revealed that both FBM and ABM had a higher proportion of S-phase (21.7 and 11.5% respectively), compared to PB and CB cells (1.2% and 2.8% respectively). FBM and ABM also showed a higher proportion of cells in the $G_2$-M phase (6.4 and 2.6% respectively) compared with PB and CB (1.7 and 1.2% respectively).These data show that FBM has the highest number of proliferating cells. The ontogenic differences were studies in stromal cells derived from FBM, ABM and CB, with a special focus on the expression of selected cytokines such as CSF, GM-CSF, G-CSF, M-CSF, IL3, IL6, IL10 and IL11. FBM showed the highest levels of expression of CSF, IL6 and IL11, when compared to other sources. These cytokines may have an important role in engraftment and homing of stem cells. The levels of expression of the other cytokines were similar in all sources of stromal cells. The levels of expression of the other cytokines were similar in all sources of stromal cells, with the exception of G-CSF, which was not detected in CB. Moreover, the number of colonies of FBM and ABM cells were higher when inoculated with fetal stromal cells. These results suggest an important regulatory role of cytokines in ontogeny of hematopoiesis. Results indicate that ewach source of hematopoietic and stromal cells has intrinsic properties, closely related to ontogenic age, which is a vital determinant of phenotypic characteristics, lineage commitments, immunogeneicity as well as proliferative potential. FBM is the best source of stem cells for the engraftment and therapeutic reconstitution due to its very high proliferative capacity, low immunogenicity and highest number of primitive stem/progenitor cells. Fetal bone marrow stem cells retrieved at their optimal stage of hematopoiesis (16-20 weeks) may be the cells of choice for both therapeutic cellular reconstitution, regeneration and gene targeting.

The compositions of the present invention may be useful in treatment of infants with sickle cell anemia. This condition may also be treated before birth fetuses that had been diagnosed in utero as well as various hemoglobinopathies, immunodeficiencies and metabolic diseases.

Furthermore, "bone paste" consisting of chips of fetal bone containing some fetal hematopoietic tissue from 16-20 weeks miscarriages, mixed with a special preparation of biodegradable organic components to form a "putty-like" material (low immunogenic potential) can be used for fracture non-unions, inborn bone defects, spinal fusions in vertebral column defects, and in any post-trauma skeletal lesions. Currently available products use inorganic or bovine-derived materials that provide a foreign matrix for bone growth.

The bone paste consists of small particles of fetal cartilage, fetal bone marrow that is rich in stromal and mesenchymal cells, cytokines and a high volume of fetal hematopoietic stem cells. This mixture also contains media and dissolvable biologic non-immunogenic support material that gives it the proper consistency. The major advantage of the support material is that it serves as a temporary non-synthetic scaffold that has proper plasticity and does not compress the underlying tissue. The support material is absorbed within a week to 10 days, without any evidence of immunogenic reaction. The bone paste can be molded to the size and shape of any lesion. Rapid vascularization and formation of a vascular network occurs in the area of application of the bone paste within 3-5 days post surgery. This is followed by infiltration of a large volume of fibroblasts, transformed subsequently into chondro- and osteoblasts. Complete healing without scarring occurred within 2-3 weeks in utero. The unique properties of fetal tissue were evident in many allogenic transplantations that were carried out. Application of allogeneic fetal cells to adults however could induce some host immune reaction, which would require a low level of immunosuppression.

The use of fetal bone paste was modeled in many allogeneic transplantations in human primates, which most closely resemble humans in terms of anatomy, physiology and immunology. The results obtained indicate that the paste may be applied to treatments of various congenital and post-trauma skeletal lesions as well as to degenerative bone and joint diseases. The paste can be modified with fetal bone marrow-derived mesenchymal cells for the treatment of soft tissues (eg myocardial ischemic diseases).

The present invention also provides an improved cryopreservative solution to improve survival of delicate fetal cells during freezing and long-term cryostorage. See below in Section on Examples for details.

Diseases or Disorders that can be treated by Hematopoietic stem cells derived from second trimester miscarriages—The product of the invention may be used in the reconstruction of inborn genetic defects, congenital defects, post-trauma lesions including combat wounds, correction of congenital or post-natal deformities. The material can also be use in reconstructive and cosmetic surgery as well as correction of surgically-induced defects such as those encountered in cancer surgery (eg, head and neck cancers) and the following diseases:

I. Diseases resulting from a failure or dysfunction of normal blood cell production and maturation including hyperproliferative stem cell disorders, aplastic anemia, pancytopenia, agranulocytosis, thrombocytopenia, red cell aplasia, Blackfan-Diamond syndrome due to drugs, radiation, or idiopathic infection;

II. Hematopoietic malignancies, acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkins's lymphoma;

III. Immunotherapy in patients with malignant, solid tumors such as malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma;

IV. Autoimmune diseases such as rheumatoid arthritis, diabetes type I, chronic hepatitis, multiple sclerosis, systemic lupus erythematosus;

V. Genetic (congenital) disorders—anemias, familial aplastic Fanconi's syndrome, Bloom's syndrome, pure red cell aplasia (PRCA), congenital dyskeratosis congenital, Blackfan-Diamond syndrome, congenital dyserythropoietic syndromes I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria G6PD (glucose-6-phosphate dehydrogenase) variants, congenital 1,2,3 pyruvate kinase deficiency congenital erythropoietin sensitivity, sickle cell disease and trait thalassemia alpha, beta, gamma met-hemoglobinemia, congenital disorders of immunity severe combined immunodeficiency disease (SCID), bare lymphocyte syndrome, ionophore-responsive combined immunodeficiency, combined immunodeficiency with a capping abnormality nucleoside phosphorylase deficiency, granulocyte actin deficiency, infantile agranulocytosis, Gaucher's disease adenosine deaminase deficiency, Kostmann's syndrome, reticular dysgenesis, congenital leukocyte dysfunction syndromes;

VII. Degenerative diseases—a) Neuorologic degenerative diseases including but not limited to Parkinson's disease, amytrophic lateral sclerosis (ALS), Alzheimer's disease and stroke; b) Ischemic cardiac diseases including myocardial infarction, cardiomyopathy and valve deficiencies VII. Others severe maladies including osteopetrosis myelosclerosis, acquired hemolytic anemias, acquired immunodeficiencies, infectious disorders causing primary or secondary immunodeficiencies, fungal infections disorders that involve disproportions in lymphoid cell sets, and impaired immune functions due to aging phagocyte disorders Kostmann's agranulocytosis chronic granulomatous disease Chediak-Higachi syndrome, neutrophil actin deficiency, neutrophil membrane GP-180 deficiency, metabolic storage diseases such as mucopolysaccharidoses and mucolipidoses, as well as miscellaneous disorders involving immune mechanisms, such as Wiskott-Aldrich Syndrome, alpha 1-antitrypsin deficiency. While not a preferred embodiment, the product of the present invention may be used in regenerative medicine to prevent or treat aging related tissue damage.

5. EXAMPLES

What makes the present invention unique is the use of fetal tissue/cells from second trimester spontaneously aborted fetuses. Healthy tissue is collected from selected donors utilizing similar methods that have been established by NIH for the collection of cord blood and according to FDA regulations applied for the use of human stem cells. This source of stem cells is defined by NIH as Pathology material and consequently falls under the so-called Exemption 4 of IRB regulations, which exempts the collection of the material from the requirement of IRB protocols. Perhaps most important, the tissues are not controversial and are free from ethical or moral burdens since they are considered as cadaveric tissue and their use is very similar to cadaveric organ transplants. The details of selection of donors and quality control issues are described below.

Considerable experience and planning are needed in the process of selecting patients/donors based on the assessment of the clinical history. All the collaborating hospitals are supplied with a package describing the benefits of fetal tissue transplantation to the mother and a tissue donation informed consent form. It also contains a uniform, specially designed chart for the medical staff to determine the suitability of the donor. This chart includes the medical and family history of the mother and the history of the pregnancy, with special focus on the viability of the lost pregnancy and the time of the fetal death before the delivery. This chart is be modeled on the one that is utilized by cord blood banks, but our chart will also include the information that is routinely collected to document the history and diagnosis of miscarriages. The medical history of the maternal donor will be established to reduce the risk of transmittance of infectious and/or malignant diseases. The history of the maternal donor will be obtained at the hospital by the attending physician and the following questions will be posed to determine a basis for exclusion:
1. History of genetic blood diseases
2. Current or past active infections in a chronic state, degenerative, infectious, neurological diseases
3. Risk factors for transmitting HIV or viral hepatitis virus
4. History of intravenous drug abuse.
5. Sexual behavior (prostitutes, bisexual etc.).
6. History of hemophilia, syphilis or gonorrhea Further, the evaluation of maternal health by the hospital, as part of their perinatal care, includes screening for various diseases such as HIV-1, HTLV-3, CMV, EBV, Parvovirus-B, Herpes Simplex I and II, Hepatitis B and C, human papilloma Type I, *Toxoplasma gondii*, Rubella, Syphilis and gonorrhea. These diseases are all included in the exclusion criteria form attached to Maternal Consent.

In all cases, the names of the donors will not be included in the records to avoid any identification of the specimen on the basis of the family name or by any other form of patient identification according to Federal regulations on the protection of human subjects.

Collection of Fetal Tissue—The fetal tissues collected from collaborating hospitals provide tissues from multiethnic (Hispanic, Oriental and African Americans and Caucasian) populations. In all of the network hospitals, patients with the diagnosis of eminent premature delivery, and who are also free of disease, are asked to sign an informed consent form after health evaluation. When hospital tests are inconclusive, additional tests are performed. The fetal age is be estimated on the basis of last maternal menstruation date and on routine sonographic measurements of the crown length and femoral length. The suitability of specimens for transplantation will be established on the basis of a complete medical history and appropriate laboratory tests taken, including sonographic examination. Special attention is paid to avoid any subject/specimen identification, which could identity the donors. When spontaneous abortion is imminent, with the consent of the mother, arrangements are made about the ossibilities of cadaveric collection. Prior to collection of the aborted tissues, the potential donors are evaluated and the cause of their miscarriage determined.

Tissue Retrieval and Short-Term Preservation

After screening of potential donors and obtaining consent from healthy mothers immediately following spontaneous loss of pregnancy, the fetus is washed with sterile normal saline and removed to a sterile area adjacent to the operating suite. It is examined by an attending physician with experience in the dysmorphology of early fetuses. Photographs are taken. All subsequent handling of the fetal tissues will be done utilizing sterile techniques. Following gross physical examination, harvesting of fetal tissues will be carried out.

All bones that contain a significant amount of bone marrow such as fetal long bone, iliac bones, scapula, sternum and ribs are removed and scraped of muscles, tendons and periosteum. The long bones are cut transversely and the bone marrow is washed out with standardized medium and placed with remaining bone fragments in the same sterile cold packs packed on wet ice in insulated boxes at 4° C. for transportation.

Quality Control of Aborted Tissues

All the specimens are subjected to stringent quality control, as described earlier. When hospital tests are inconclusive, a small portion of the cells from each sample will be used independently for screening for bacteriological, viral, fungal contaminations. The remaining major portion of the cells are processed for cryopreservation. In the event of detection of any contamination by infectious agents and/or genetic aberrations, the stored specimens are discarded suitably. Fluorescence In Situ Hybridization (FISH), for rapid detection of aneuploidy in nondividing (interphase) cells and standard cytogenetic analysis are for exclusion of genetically unsuitable tissues, such as trysomies. Screening for various metabolic diseases such as micropolysaccharidoses I-VII, mucolipidoses (adreno-, metachromatic-, global cell-leukodystrophies), type III Goucher diseases, Leach-Nyhan syndrome, Wolmah syndrome, mannosidosis, and fucosidosis are screened by enzyme assays according to NIH Cord Blood protocol.

Aliquots of cell suspensions from the tissue samples are tested for bacterial and fungal contaminants. The cell suspensions are cultured on blood agar and Sabourauds agar plates. The blood agar plates are incubated both at 37° C. and 20° C. for aerobic conditions, and at 37° C. in $CO_2$ for anaerobic conditions to detect gram negative and gram positive bacterial contaminants. The incubation time for the plates at 37° C. will be 48 hours. Screens for major viral infections are utilized to eliminate the possibility of viral contamination.

Evaluation of Collected Tissues—

The viability of all processed healthy tissues is established by trypan blue dye exclusion assay before long-term storage by trypan blue dye exclusion assay. According to our earlier experience with fetal bone marrow, successful engraftment was obtained with tissues that were 80% viable by this criterion (after 6 mos. storage in freezing solution with 10% DMSO) The functional quality of the tissues will be evaluated by "colony forming unit" analysis (CFU-analysis). These two methods are utilized for periodic (every 6 months) evaluation of the cryopreserved tissues.

Cryopreservation of fetal cells and tissues. Cryopreservation of fetal stem cells is carried out using a cocktail consisting of Normosol media, (although RPMI-1640 media can be used just as well), 4-5% human serum albumin (HSA), 1-2.5% dimethyl sulfoxide (DMSO) and 1-2.5% Dextran. It is critical for high recovery and viability of the cells that the DMSO concentration does not go beyond 2.5%. Although it is customary to add an antibiotic mix (2% PSNG) to the freezing cocktail, we removed that from our cocktail because of the potential allergenic characteristics of some antibiotics. The antibiotics will be used only in "complete media" during processing of the cells. The cell suspension is aliquoted into freezing vials (4-10×$10^6$ cells/vial). Freezing is carried out using step-down freezing methods, where the cells suspension is initially cooled to 15° C. then to 4° C. then to 0° C., then lowered to −30° C. and then ramped down to liquid nitrogen temperature (−180° C.) over a period of 30 min. Thawing of frozen cells is also done slowly, although this step is not as critical as the freezing. All cells were tested before freezing and after thawing by the trypan blue exclusion assay, phenotypic analysis by flow cytometry, and functional characterization by CFU-C (colony forming unit in culture) assays before and after freezing. The viability of the fetal cells after months of cryopreservation followed by thawing was at least 90%.

Preparation of Bone Paste—The preparation of the bone paste requires careful screening of donor tissue (as described above) to prevent the transmission of bacterial, fungal, viral or genetic contaminants. The novelty of our bone paste is based on it fully biological nature, in contrast to other materials that are used for bone healing that contain inorganic scaffolds or synthetic support matrices. The bone paste consists of organic, biodegradable material mixed with human, non-immunogenic fetal bone tissue. Moreover the bone paste has adhesive properties and can be molded to any desired size and shape of the lesion. Small particles (~5 mm) of fetal bone are prepared manually and are mixed with biodegradable agar and tissue culture medium. The latter is Dulbecco's medium without L-glutamine but enriched with glucose. The bone chips are obtained from fetal long bones and cut manually into small particles at room temperature. At this age of skeletal development (16-22 weeks of gestation) the fetal long bones exhibit large intramedullary cavities with a large volume of marrow. It is surrounded by thin layers of cortical palate. Consequently the bone chips contain a large proportion of bone marrow stem cells such as hematopoietic and stromal (mesenchymal) cell populations that are rich in cytokines. The cartiliginous cortical plate consists of a small volume of fibroblasts, chondroblasts and osteoblasts. Rapid proliferation and differentiation of fetal cells, together with the agar plus medium stimulate rapid vascularization and chondro/osteogenesis in the area. The unique healing properties of fetal tissue provide complete reconstruction of the lesion in about 10 days. Our bone paste is one of the first examples of cell engineering.

The proportions of the three principal component of the bone paste are critical for successful application. Fetal bone chips: 30-40% by volume, 10% medium and the balance is agar. Departure from these proportions leads to a material that cannot be molded properly and does not have adhesive properties. The allogeneic fetal bone paste described above is made exclusively from cryopreserved material because of the requirements for quality controls preclude the use of fresh tissue. The viability of cells from our method of cyopreservation is very high (>90%). One of the very important aspects of this material is that it is not immunogenic and does not induce graft-versus-host disease. Thus the patients may need very minimal (or no) immunosuppression. The bone paste can also be made from autologous bone. However, in that case the healing process is much slower and generally not satisfactory.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A method for preparing bone paste from fetal bone chips collected from human fetal tissue from second trimester miscarriages (16-20 weeks of gestation), wherein the fetal bone chips contain hematopoietic stem or progenitor cells and stromal (mesenchymal) cells, said method comprising:
    (a) collecting the fetal bone chips;
    (b) cryopreserving the fetal bone chips utilizing a non-toxic cryopreservation cocktail consisting of 1 to 2.5% dimethyl sulfoxide, 4-5% human serum albumin and 1-2.5% dextran in RPMI medium; and
    (c) thawing the cryopreserved fetal bone chips, such that the stem or progenitor cells are at least 90% viable using said cryopreservation cocktail,
    wherein the method further comprises the step of mixing the thawed fetal bone chips, 30-40% by volume, with 10% medium and the balance with agar in an appropriate matrix to produce a bone paste.

* * * * *